United States Patent
Fowler

(10) Patent No.: US 6,858,200 B2
(45) Date of Patent: Feb. 22, 2005

(54) SUNSCREEN FORMULATIONS

(75) Inventor: Kevin Fowler, Millington, TN (US)

(73) Assignee: Schering-Plough Healthcare Healthcare Products Inc., Memphis, TN (US)

(*) Notice: Subject to any disclaimer, the term of this patent is extended or adjusted under 35 U.S.C. 154(b) by 353 days.

(21) Appl. No.: 10/164,720

(22) Filed: Jun. 6, 2002

(65) Prior Publication Data

US 2002/0197292 A1 Dec. 26, 2002

Related U.S. Application Data

(60) Provisional application No. 60/296,433, filed on Jun. 6, 2001.

(51) Int. Cl.$^7$ ............................ A61K 7/42; A61K 7/44; A61K 7/00
(52) U.S. Cl. ............................ 424/59; 424/60; 424/400; 424/401; 514/937; 514/938; 514/939
(58) Field of Search ............................ 424/59, 60, 400, 424/401; 514/937, 938, 939

(56) References Cited

U.S. PATENT DOCUMENTS

| 6,391,290 B1 | 5/2002 | Fowler | 424/59 |
| 6,488,916 B1 | 12/2002 | Fowler | 424/59 |

OTHER PUBLICATIONS

"Transferring Proven Polymer Technology to the Global . . . ", New Phase Technologies, (1998).

*Primary Examiner*—Shelley A. Dodson
(74) *Attorney, Agent, or Firm*—Robert J. Lipka

(57) ABSTRACT

Disclosed are formulations for topical application, the formulation comprising a $C_{15}$ branched polyalphaolefin, an aqueous phase, a non-aqueous phase, and at least one sunscreen active agent, alone or in combination with an insect repellant.

23 Claims, No Drawings

SUNSCREEN FORMULATIONS

CROSS REFERENCE TO RELATED APPLICATION

This application claims formal benefit of priority to U.S. Provisional Patent Application 60/296,433, filed Jun. 6, 2001.

BACKGROUND OF THE INVENTION

It is now generally recognized that exposure to solar radiation can have adverse health consequences, sometimes not appearing until several years following the exposure. Of course, the immediately appearing "sunburn" from an overexposure can itself be a serious acute health problem.

Many products are available to reduce the amount of solar ultraviolet radiation received by the skin during exposure to the sun's rays. Typical product formulations are lotions, creams, ointments or gels containing chemical and/or physical barriers to ultraviolet transmission. These vary considerably in their abilities to protect the skin against the physical and is biochemical effects of ultraviolet radiation.

Earlier sunscreening formulations were designed to protect against sunburn from a limited solar exposure period, while transmitting sufficient radiation to permit skin tanning. However, the current focus is on eliminating as much ultraviolet exposure as possible, it being recognized that skin tanning, while esthetically pleasing to some, is a clear indication of tissue damage from overexposure to solar radiation. It has been recently discovered that any amount of unprotected exposure can potentially cause immune system suppression and lead to future health problems, such as skin carcinomas and other dermatological disorders.

The SPF (Sun Protection Factor) rating system has been developed to provide consumer guidance in selecting suitable sunscreens for any given outdoor activity. In general, the SPF number approximately corresponds to the multiple of time during which the properly applied sunscreen will prevent obvious reddening of the skin, over the exposure time that causes unprotected skin to exhibit reddening. Thus, if an SPF 8 sunscreen formulation has been properly applied, a person should be able to remain in the sun without visible effects for eight times the usual unprotected duration. Of course, the duration of unprotected exposure which produces a visible effect on the skin varies from one individual to another, due to differences in their skin cells. Currently popular are high-SPF "sunblocker" products, having SPF values of at least 30.

Most of the commercially available sunscreen formulations are not well suited for use by those engaged in strenuous outdoor activities, such as construction work, gardening, athletic events and many others, due to the tendency for perspiration from the body to interact with the applied formulation. For example, perspiration, or moisture from other sources, including rain, can cause sunscreen active ingredients and other irritating components of the formulation to enter the eyes and cause discomfort. It is also frequently detrimental, particularly in activities such as tennis which require a reliable grip on equipment, to have an applied sunscreen formulation remain lubricious after application or become lubricious when mixed with perspiration or other moisture.

It is advantageous to have a suncare formulation that is waterproof. Waterproof formulations allow the user to engage in activities such as swimming while still being protected against ultraviolet radiation. Hydrophobic materials typically serve as waterproofing agents that impart film forming and waterproofing characteristics to an emulsion. However, there is still a need for products having physical attributes that display improved waterproof performance, and that have a reduction in migration of the formulation across the formulation wearer's skin.

A sunscreen product which has been available for several years, but which does not exhibit disadvantages such as the foregoing, is sold by Schering-Plough HealthCare Products, Inc., Memphis, Tenn. U.S.A. as COPPERTONE™. SPORT™. SPF 30 lotion. This product contains the active ingredients octyl salicylate, octyl methoxycinnamate and oxybenzone, totaling 17.5 weight percent of the formulation, and is an oil-in-water emulsion formulated with 1.5 weight percent of a fumed silica having a hydrophobic surface treatment. It is thought that the silica serves to immobilize the active agents in the internal phase of the formulation and inhibit their migration under the influence of skin oils and/or external moisture. The product also has a very desirable "dry" feel as it is being applied, quite unlike the very liquid nature of the usual lotion which does not contain particulate ingredients other than those approved for use as sunscreen active ingredients.

There is a need for products having physical attributes as those of the Coppertone Sport SPF 30 product, but which have more predictable formulation behavior and stability.

SUMMARY OF THE INVENTION

Accordingly, there is disclosed an emulsion formulation for topical application to the skin comprising: an aqueous phase, an oil phase, at least one emulsifier, and a highly branched $C_{15}$ polyalphaolefin having a molecular weight of about 1000 to 2000, a polydispersity of molecular weight to molecular number of about 0.01 to about 5, wherein the polyalphaolefin has water proofing capabilities.

Also disclosed is an emulsion formulation for topical application to the skin comprising: an aqueous phase, an oil phase, at least one emulsifier, an epichlorohydrin cross-linked glyceryl starch, a highly branched $C_{15}$ polyalphaolefin having a molecular weight of about 1000 to 2000, a polydispersity of molecular weight to molecular number of about 0.01 to about 5, wherein the polyalphaolefin has water proofing capabilities, and at least one sunscreen active agent.

Also disclosed is an after sun emulsion formulation for topical application to the skin comprising an aqueous phase, an oil phase, at least one emulsifier, a highly branched $C_{15}$ polyalphaolefin having a molecular weight of about 1000 to 2000, a polydispersity of molecular weight to molecular number of about 0.01 to about 5, wherein the polyalphaolefin has water proofing capabilities.

Also disclosed in an emulsion formulation for topical application to the skin comprising an aqueous phase, an oil phase, at least one emulsifier, a highly branched $C_{15}$ polyalphaolefin having a molecular weight of about 1000 to 2000, a polydispersity of molecular weight to molecular number of about 0.01 to about 5, wherein the polyalphaolefin has water proofing capabilities, and an insect repellant.

Also disclosed is an emulsion formulation for topical application to the skin comprising an aqueous phase, an oil phase, at least one emulsifier, a highly branched $C_{15}$ polyalphaolefin having a molecular weight of about 1000 to 2000, a polydispersity of molecular weight to molecular number of about 0.01 to about 5, wherein the polyalphaolefin has water proofing capabilities, a sunscreen active agent and an insect repellant.

Also disclosed is an emulsion formulation for topical application to the skin comprising an aqueous phase, an oil phase, at least one emulsifier, a highly branched $C_{15}$ polyalphaolefin having a molecular weight of about 1000 to 2000, a polydispersity of molecular weight to molecular number of about 0.01 to about 5, wherein the polyalphaolefin has water proofing capabilities, and a sunless tanning agent.

DETAILED DESCRIPTION OF THE INVENTION

Names given to chemical substances herein generally are either accepted chemical names, or are trade organization or regulatory agency approved names such as CTFA Adopted Names as listed in J. M. Nikitakis et al., Eds., CTFA International Cosmetic Ingredient Dictionary, Fourth Ed., The Cosmetic, Toiletry and Fragrance Association, Washington, D.C., 1991.

The term "percent by weight" as used herein means the percent by weight of the ingredient per weight of the overall formulation.

Suitable water proofing agents of the present invention include a branched polyalphaolefin polymer that is constructed from $C_{15}$ branched chain. Preferably, the agent is a liquid at room temperature. This is advantageous because the solution does not require heating during formulation, thus avoiding the potential destruction of other ingredients that have lower melting points. The polymer should have a molecular weight of about 1500, and a polydispersity of about 1 to 5, more preferably 3. It should have a viscosity in cP at 99 degrees Celsius of about 795. Most preferably, the $C_{15}$ highly branched polyalphaolefin is available under the trade name of Performa V 825 from New Phase Technologies, a subsidiary of Petrolite, which is a subsidiary of Baker Hughes. Surprisingly, and unlike other waterproofing polymers, the Performa V 825 polymer does not leave an after feel that is tacky or sticky.

The term "molecular weight" as used herein is the definition known by one of skill in the art. More specifically, it is the average molecular weight of the polymers. The term "molecular number" as used herein is the definition known by one of skill in the art. More specifically, it is the average molecular number of the polymers. The term "polydispersity" as used herein is the definition known by one of skill in the art, and is defined as molecular weight ("MW") divided by molecular number ("MN"), or MW/MN.

The term "emulsion" shall be used herein to identify oil-in-water or water-in-oil type dispersion formulations intended for application to the skin, particularly lotions and creams providing cosmetic or therapeutic benefits. The emulsions may contain any of a number of desired "active" ingredients, including, inter alia, skin colorants, drug substances (such as anti-inflammatory agents, antibiotics, topical anesthetics, antimycotics, keratolytics, etc.), skin protectants or conditioners, humectants, ultraviolet radiation absorbers, sunless tanning agents, insect repellants and the like, depending on the intended uses for the formulations.

The present invention is not dependent upon any particular formulation technique, it being recognized that the choice of specific formulation components may well make necessary some specific formulation procedure.

Suitable emulsifiers for one aspect of the invention are those known in the art for producing oil-in-water and/or water-in-oil type emulsions. An aqueous external phase is preferred by many people for skin contact, since it is not as likely to produce an oily or greasy sensation when it is being applied, as is an emulsion having an oil external phase. The typical oil-in-water emulsifier has a hydrophilic-lipophilic balance (frequently abbreviated as "HLB") value greater than about 9, as is well known in the art; however, this "rule" is known to have numerous exceptions. The chosen emulsifier, depending upon its chemical nature, will be a component of either the oil or aqueous phase, and assists with both the formation and the maintenance, or stability, of the emulsion.

Most of the widely used oil-in-water emulsifier systems for sunscreen formulations can be used in the invention. Particularly preferred emulsifiers are PEGS distearate available under the trade name of Emerest 2712 from Henkel, PEG-5 glyceryl stearate available under the trade name POEM-S-105 from Riken Vitamin Oil, PEG-6 hydrogenated castor oil, PEG-6 Oleate, available under the trade name STEPAN PEG-300 MO from Stepan, sorbitan sesquioleate, available under the trade name Arlacel 83 and Arlacel C from ICI Surfactants, TEA-stearate, available under the trade name of Cetasal from Gattefosse S.A. The amount of emulsifier used in the present invention is present in an amount of about 0.05 to about 20% by weight Suitable emulsifiers for another aspect of the invention are those known in the art for producing water-in-oil type emulsions. The typical water-in-oil emulsifier has a HLB value of about 4 to about 6, as is well known in the art; however, this "rule" is also known to have numerous exceptions. Selection of suitable water-in-oil emulsifiers is well known in the formulation art. Particularly preferred water-in-oil type emulsifiers that may be employed include sorbitan triisostearate available under the trade name Crill 65 from Croda Oleochemicals, and polyglyceryl-3 distearate available under the trade name Cremophor GS32 from BASF.

For purposes of the present invention, a "sunscreen active agent" shall include all of those materials which are regarded as acceptable for use as active sunscreening ingredients. Approval by a regulatory agency is generally is required for inclusion of active agents in formulations intended for human contact, and those active agents which have been or are currently approved for sunscreen use in the United States include, without limitation, para aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, and/or red petrolatum.

It is typical to use combinations of two or more sunscreen ingredients in a formulation, to achieve higher levels of ultraviolet absorption or to provide useful absorption over a wider range of ultraviolet wavelengths than can be the case with a single active component.

Several other sunscreen active ingredients are accepted for use in other countries and are also considered to be within the scope of the present invention.

For purposes of the present invention, the amount of sunscreen active agent or agents that will be present will conform to such amounts as are set forth in the FDA monograph for such sunscreen agents.

Insect repelling components are also a desirable ingredient in sunscreen formulations, since the formulations are normally used primarily by persons engaged in outdoor activities. The most widely used active agent for personal care products is N,N-Diethyl-m-toluamide, frequently called "DEET" and available in the form of a concentrate containing at least about 95 percent DEET. Other synthetic chemical repellents include dimethyl phthalate, ethyl hexanediol, indalone, di-n-propylisocinchoronate, bicycloheptene, dicarboximide and tetrahydrofuraldehyde. Certain plant-derived materials also have insect repellent activity, including citronella oil and other sources of citronella (including lemon grass oil), limonene, rosemary oil and eucalyptus oil. Choice of an insect repellent for incorporation into the sunscreen emulsion will frequently be influenced by the odor of the repellent. The amount of repellent agent used will depend upon the choice of agent; DEET is useful at high concentrations, such as up to about 15 percent or more, while some of the plant-derived substances are typically used in much lower amounts, such as 0.1 percent or less. The formulations of the present invention are particularly useful as insect repellants because they do not penetrate the skin.

The compositions of the present invention may contain a wide range of additional, optional components. The CTFA Cosmetic Ingredient Handbook, Eight Edition, 2000, which is incorporated by reference herein in its entirety, describes a wide variety of cosmetic and pharmaceutical ingredients commonly used in skin care compositions, which are suitable for use in the compositions of the present invention. Examples of these functional classes include: absorbents, abrasives, anticaking agents, antifoaming agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous).

Water may be employed in amounts effective to form the emulsion. It is generally preferred to use water which has been purified by processes such as deionization or reverse osmosis, to improve the batch-to-batch formulation inconsistencies which can be caused by dissolved solids in the water supply. The amount of water in the emulsion or composition can range from about 15 percent to 95 weight percent.

An emollient is an oleaginous or oily substance which helps to smooth and soften the skin, and may also reduce its roughness, cracking or irritation. Typical suitable emollients include mineral oil having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural sonora jojoba oils, safflower oil, corn oil, liquid lanolin, cottonseed oil and peanut oil. Preferably, the emollient is a cocoglyceride, which is a mixture of mono, di and triglycerides of cocoa oil, sold under the trade name of Myritol 331 from Henkel KGaA, or Dicaprylyl Ether available under the trade name Cetiol OE from Henkel KGaA or a $C_{12}$–$C_{15}$ Alkyl Benzoate sold under the trade name Finsolv TN from Finetex. One or more emollients may be present ranging in amounts from about 1 percent to about 10 percent by weight, preferably about 5 percent by weight.

Other suitable emollients include squalane, castor oil, polybutene, odorless mineral spirits, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of ($C_{12}$–$C_{15}$) alcohols, the octanoates and decanoates of alcohols and polyalcohols such as those of glycol and glycerol, ricinoleates esters such as isopropyl adipate, hexyl laurate and octyl dodecanoate, dicaprylyl maleate, hydrogenated vegetable oil, phenyltrimethicone, jojoba oil and aloe vera extract.

Other suitable emollients which are solids or semi-solids at ambient temperatures may be used. Such solid or semi-solid cosmetic emollients include hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the formulation.

A humectant is a moistening agent that promotes retention of water due to its hygroscopic properties. Suitable humectants include glycerin, polymeric glycols such as polyethylene glycol and polypropylene glycol, mannitol and sorbitol. Preferably, the humectant is Sorbitol, 70% USP or polyethylene glycol 400, NF. One or more humectants can optionally be included in the formulation in amounts from about 1 to percent about 10 percent by weight, preferably about 5 percent by weight.

A dry-feel modifier is an agent which when added to an emulsion, imparts a "dry feel" to the skin when the emulsion dries. Dry feel modifiers that can be used in addition to the Performa V 825 as used in the formulation of the present invention include talc, kaolin, chalk, zinc oxide, silicone fluids, inorganic salts such as barium sulfate, surface treated silica, precipitated silica, fumed silica such as an Aerosil available from Degussa, and an epichlorohydrin cross-linked glyceryl starch that is available from National Starch currently, currently sold under the tradename of Vulca 90.

A waterproofing agent is a hydrophobic material that imparts film forming and waterproofing characteristics to an emulsion. A suitable waterproofing agent may be, for instance, a copolymer of vinyl pyrollidone and eicosene monomers such as Ganex V 220 Polymer, trade name of ISP Inc., which can be used as an additional waterproofing agent in combination with the Performa V 825 polymers as set forth above. Another suitable waterproofing agent is a mixture of a homopolymer of acrylic acid cross-linked with an allyl ether of pentaerythritol, an allyl ether of sucrose or an allyl ether of propylene, available under the tradename of Carbopol Ultrez 10 available from Goodrich. The waterproofing agent is used in amounts effective to allow the sunscreen to remain effective on the skin after exposure to circulating water for at least 80 minutes using the procedures described by the U.S. Food and Drug Administration in "Sunscreen Drug Products for OTC Human Use," Federal Register, Vol. 43, Aug. 25, 1978, Part 2, pp. 38206–38269.

An antimicrobial preservative is a substance or preparation which destroys, or prevents or inhibits the proliferation of, microorganisms in the sunscreen composition, and which may also offer protection from oxidation. Preservatives are frequently used to make self-sterilizing, aqueous based products such as emulsions. This is done to prevent the development of microorganisms that may be in the product from growing during manufacturing and distribution of the product and during use by consumers, who may further inadvertently contaminate the products during normal use. Typical preservatives include the lower alkyl esters of para-hydroxybenzoates (parabens), especially methylparaben, propylparaben, isobutylparaben and mixtures thereof, benzyl alcohol, phenyl ethyl alcohol and benzoic acid. The preferred preservative is available under the trade name of Germaben II from Sutton. One or more antimicrobial preservatives can optionally be included in the in an amount ranging from about 0.001 to about 10 weight percent, preferably about 0.05 to about 1 percent.

An antioxidant is a natural or synthetic substance added to the sunscreen to protect from or delay its deterioration due to the action of oxygen in the air (oxidation). Anti-oxidants prevent oxidative deterioration which may lead to the generation of rancidity and nonenyzymatic browning reaction products. Typical suitable antioxidants include propyl, octyl and dodecyl esters of gallic acid, butylated hydroxyanisole (BHA, usually purchased as a mixture of ortho and meta isomers), butylated hydroxytoluene (BHT), nordihydroguaiaretic acid, Vitamin A, Vitamin E and Vitamin C. One or more antioxidants can optionally be included in the sunscreen composition in an amount ranging from about 0.001 to about 5 weight percent, preferably about 0.01 to about 0.5 percent.

Chelating agents are substances used to chelate or bind metallic ions, such as with a heterocylic ring structure so that the ion is held by chemical bonds from each of the participating rings. Suitable chelating agents include ethylene diaminetetraacetic acid (EDTA), EDTA disodium, calcium disodium edetate, EDTA trisodium, EDTA tetrasodium and EDTA dipotassium. One or more chelating agents can optionally be included in the sunscreen in amounts ranging from about 0.001 to about 0.2 weight percent preferably about 0.01% weight percent.

Fragrances are aromatic substances which can impart an aesthetically pleasing aroma to the sunscreen composition. Typical fragrances include aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modem trend is to use synthetically prepared fragrances, particularly in high-volume products.

A pH modifier is a compound that will adjust the pH of a formulation to a lower, e.g., more acidic pH value, or to a higher, e.g., more basic pH value.

The formulations of the invention are waterproof. The formulations of the invention can serve as sunscreen formulations. The formulations of the invention prevent the sunscreen active agent from migrating across the skin's surface. This property is especially beneficial for application of the formulation to the face where it is desirable to keep sunscreens from migrating into the eye from the surrounding facial areas. The formulations of the invention also prevent partitioning of the invention into deeper layers of the stratum corneum, another heretofore unseen benefit of the formulations of the present invention.

The formulations of the present invention may also contain sunless tanning agents. It has long been known that certain compounds form pigments when applied to the skin. Products containing dihydroxyacetone (frequently simply abbreviated "DHA") have been marketed since the early 1960's, and have been found satisfactory by many persons who wish to give their skin the appearance of an attractive tan, but do not desire to risk the now well-appreciated health hazards of exposure to solar or artificially-generated ultraviolet radiation.

However, some persons have not obtained the desired results from DHA applications. A small number of individuals develop a coloration which tends to appear yellowish or orange. Some others, probably due to perspiration, rubbing or washing during the slow generation of color as skin components react with DHA, or to a lack of care to evenly apply the DHA, develop uneven coloration.

The chemistry of DHA-skin interaction has been investigated by several workers. Wittgenstein and Berry published a paper "Reaction of Dihydroxyacetone (DHA) with Human Skin Callus and Amino Compounds," in *The Journal of Investigative Dermatology*, Vol. 36, pages 283–286 (1961), describing work to characterize the browning phenomenon. They reported that DHA reacts with a number of compounds, including ammonia and amino acids, to form a brown color, and theorized that skin browning is due to the reaction of DHA with free amino groups in the skin, the amino groups probably being on arginine molecules which are present in skin proteins.

A. Meybeck published "A Spectroscopic Study of the Reaction Products of Dihydroxyacetone with Aminoacids" in *Journal of the Society of Cosmetic Chemists*, Vol. 28, pages 25–35 (1977), and characterized brown pigments formed from the reaction of DHA with amino and other acids at 100° C. Further experiments at 37° C. were conducted to better simulate reactions which may occur in the skin: DHA was reacted with the amino acids glycine, lysine, alanine, serine and arginine, but only glycine and lysine produced significant amounts of pigment after 24 hours. It was concluded that DHA must act by initially condensing with free amino acids at the skin surface, followed by polymerization and linking to proteins in the stratum corneum, probably through lysine side chains.

A further study was reported by M. F. Bobin, M. C. Martini and J. Cotte, "Effects of Color Adjuvants on the Tanning Effect of Dihydroxyacetone," *Journal of the Society of Cosmetic Chemists*, Vol. 35, pages 265–272 (1984). This work involved measuring the rate of color development after mixing DHA and various amino acids or their derivatives, and applications of DHA and methionine sulfoxide in vivo. It was concluded that methionine sulfoxide is a useful adjuvant to DHA, as the combination provided rapid color development, plus a more intense and long lasting color than would be obtained with only DHA. This result was thought to result from the affinity of methionine sulfoxide for keratin.

*Chemical Abstracts*, Vol. 95, abstract 30226g (1981) summarizes a German patent document (3,037,497) pertaining to dyeing skin, hair, feathers, fur, etc. by treating with a mixture of DHA and an amino acid sulfoxide. When DHA and methionine sulfoxide were applied in cream formulations, skin turned a deep brown color after three hours and the color was more resistant to washing than that obtained with only DHA.

Black et al., in U.S. Pat. No. 3,177,120, discussed the problem of including DHA and amino group-containing sunscreens together in a formulation, and concluded that only sunscreens free from amino groups should be used, to prevent formation of a yellow or brown color in the storage container; color formation is also said to be accompanied by inactivation of both the DHA and sunscreen.

Accordingly, sunless tanning agents in combination with Performa V 825 are also considered to be within the scope of the present invention.

The invention will be further described by means of the following examples, which are not intended to limit the invention, as defined by the appended claims, in any manner.

EXAMPLE 1

| Percent W/W | Ingredient Description |
|---|---|
| Part A | |
| 55.35 | USP Purified Water |
| 0.25 | Pemulen TR-2 |
| 4.23 | Polyethylene Glycol 400, NF |
| 1 | Germaben II |
| 0.01 | Disodium EDTA |
| Part B | |
| 7.5 | Parsol MCX or Neoheliopanav |
| 4 | Uvasorb; Uvinul M40; Escalol 567 |
| 5 | Neo Heliopan OS |
| 9 | Homomenthyl Salicylate; Homosal |
| 0.1 | Sonora Jojoba Oil |
| 0.1 | Vitamin E, DL Alpha Tocopherol |
| 0.1 | Aloe Vera Lipo-/Aloe Oil Extr. |
| 3 | Performa V 825 Polymer. |

-continued

| Percent W/W | Ingredient Description |
|---|---|
| | Part C |
| 10 | USP Purified Water |
| 0.35 | Triethanolamine, 99% NF |
| 0.45 | Cetyl Phosphate |
| | Part D |
| QS | USP Purified Water |

Add the ingredients of Part A except the Pemulen to a beaker and mix. Slowly sprinkle in the Pemulen and mix until it is completely dispersed. Add the ingredients of Part B to a second beaker and heat with mixing to 135–145 F until all the oxybenzone has dissolved. Add the oil phase to the water phase and mix with a high speed disperser for a minimum of 15 minutes. Combine the water and TEA of Part "C" and mix, then add the Colafax CPE and heat to 140–145 F while mixing until all of the ingredients have dissolved. The resulting solution should be clear. Change to a 3 blade prop and continue mixing primary emulsion of Step 03. Add the TEA/Colafax CPE solution of step 04 to the primary emulsion and mix for 3 minutes. Q.S. the batch to weight with the water and mix well.

EXAMPLE 2

| Percent W/W | Ingredient Description |
|---|---|
| | Part A |
| 71.7 | USP Purified Water |
| 0.4 | Pemulen TR-1 |
| 0.15 | Carbopol ETD 2001 |
| 0.2 | Methylparaben, NF |
| | Part B |
| 0.01 | Disodium EDTA |
| 5 | Polyethylene Glycol 400, NF |
| | Part C |
| 4 | Octocrylene |
| 5 | Neo Heliopan OS |
| 7 | Homomenthyl Salicylate; Homosal |
| 0 | Vitamin E, DL Alpha Tocopherol |
| 0.05 | Aloe Vera Lipo-/Aloe Oil Extr. |
| 0.1 | Propylparaben, NF |
| 3 | Performa V 825 Polymer. |
| | Part D |
| 1 | Benzyl Alcohol, NF |
| | Part E |
| 0.34 | Triethanolamine, 99% NF |
| | Part F |
| 2 | Starch Dry-Flo PC 28-1800 |

Using a prop mixer equipped with a small tooth blade, disperse the Pemulen and Carbopol ETD 2001 into the water of Part A using rapid mixing for five minutes, then change to a 3 prong prop and mix until free from lumps. Next, add the methylparaben and mix well. Add the ingredients of Part B to the Pemulen/Carbopol ETD 2001 solution and mix well. In a beaker equipped with a prop mixer combine the ingredients of Part C and heat to 120 F with mixing until all has dissolved. Add the oil phase of Step 3 to the aqueous phase of Step 2 and mix well. Add the benzyl alcohol of Part D to the batch of Step 4 and mix well. Add the TEA of Part E and mix vigorously until a definite emulsion occurs. Add the Starch Dry-Flo at 89.6 F to the batch of Step 6 and mix well.

EXAMPLE 3

| Percent W/W | Ingredient Description |
|---|---|
| | Part A |
| 66.7 | USP Purified Water |
| 0.4 | Pemulen TR-1 |
| 0.15 | Carbopol ETD 2001 |
| 0.2 | Methylparaben, NF |
| | Part B |
| 0.01 | Disodium EDTA |
| 5 | Polyethylene Glycol 400, NF |
| | Part C |
| 5 | Octocrylene |
| 2 | Parsol 1789 |
| 5 | Neo Heliopan OS |
| 7 | Homomenthyl Salicylate; Homosal |
| 0.05 | Vitamin E, DL Alpha Tocopherol |
| 0.05 | Aloe Vera Lipo-/Aloe Oil Extr. |
| 0.1 | Propylparaben, NF |
| 2 | Uvasorb; Uvinul M40; Escalol 567 |
| 3 | Performa V 825 Polymer. |
| | Part D |
| 1 | Benzyl Alcohol, NF |
| | Part E |
| 0.34 | Triethanolamine, 99% NF |
| | Part F |
| 2 | Starch Dry-Flo PC 28-1800 |

Using a prop mixer equipped with a small tooth blade, disperse the Pemulen and Carbopol ETD 2001 into the water of Part A using rapid mixing for five minutes, then change to a 3 prong prop and mix until free from lumps. Next, add the methylparaben and mix well. Add the ingredients of Part B to the Pemulen/Carbopol ETD 2001 solution of Step 1 and mix well. In a beaker equipped with a prop mixer, combine the ingredients of Part C and heat to 120 F with mixing until the Spectrasorb is dissolved. Add the oil phase of Step 3 to the aqueous phase of Step 2 and mix well. Add the benzyl alcohol of Part D to the batch of Step 4 and mix well. Add the TEA of Part E and mix vigorously until a definite emulsion occurs. Add the Starch Dry-Flo at 89.6 F to the batch of Step 6 and mix well. Add Part F and mix vigorously for at least 15 minutes.

EXAMPLE 4

| Percent W/W | Ingredient Description |
|---|---|
| | Part A |
| 60.85 | USP Purified Water |
| 0.4 | Pemulen TR-1 |
| 0.2 | Methylparaben, NF |

| Percent W/W | Ingredient Description |
|---|---|
| | Part B |
| 0.01 | Disodium EDTA |
| | Part C |
| 10 | Octocrylene |
| 2 | Parsol 1789 |
| 5 | Neo Heliopan OS |
| 10 | Hemomenthyl Salicylate; Homosal |
| 0.05 | Vitamin E, DL Alpha Tocopherol |
| 0.05 | Aloe Vera Lipo-/Aloe Oil Extr. |
| 0.1 | Propylparaben, NF |
| 3 | Performa V 825 Polymer. |
| | Part D |
| 1 | Benzyl Alcohol, NF |
| | Part E |
| 0.34 | Triethanolamine, 99% NF |
| | Part F |
| 5 | Polyethylene Glycol 400, NF |
| 2 | Starch Dry-Flo PC 28-1800 |

Using a prop mixer equipped with a small tooth blade, disperse the Pemulen into the water of Part A using rapid mixing for five minutes, then change to a 3 prong prop and mix until free from lumps. Next, add the methylparaben and mix well. Add the ingredients of Part B to the Pemulen/Carbopol ETD 2001 solution of Step 1 and mix well. In a beaker equipped with a prop mixer, combine the ingredients of Part C and heat to 120 F with mixing until all has dissolved. Add the benzyl alcohol of Part D to the batch of Step 4 and mix well. Add the oil phase of Step 3 to the aqueous phase of Step 2 and mix well. Add the TEA of Part E and mix vigorously until a definite emulsion occurs. While mixing the PEG-400 on a mechanical stirrer, slowly add the Starch Dry-Flo with vigorous agitation. Mix until uniform. Add the suspension of Step 07 to the batch of Step 06 with vigorous agitation. Mix until uniform.

EXAMPLE 5

| Percent W/W | Ingredient Description |
|---|---|
| | Part A |
| 56 | USP Purified Water |
| 0.25 | Pemulen TR-2 |
| -0.1 | Carbopol ETD 2001 |
| 4.23 | Polyethylene Glycol 400, NF |
| 0.2 | Methylparaben, NF |
| 0.01 | Disodium EDTA |
| | Part B |
| 2 | Parsol 1789 |
| 5 | Octocrylene |
| 4 | Uvasorb; Uvinul M40; Escalol 567 |
| 5 | Neo Heliopan OS |
| 9 | Homomenthyl Salicylate; Homosal |
| 0.05 | Sonora Jojoba Oil |
| 0.05 | Vitamin E, DL Alpha Tocopherol |
| 0.05 | Aloe Vera Lipo-/Aloe Oil Extr. |
| 3 | Performa V 825 Polymer. |
| 0.1 | Propylparaben, NF |
| | Part C |
| 10 | USP Purified Water |
| 0.35 | Triethanolamine, 99% NF |
| 0.45 | Cetyl Phosphate |
| | Part D |
| QS | USP Purified Water |

Add all ingredients of Part A except the Pemulen to a beaker and mix. Slowly sprinkle in the Pemulen/Carbopol and mix until completely dispersed. Add the ingredients of Part B to a second beaker and heat with mixing to 135–145 F. until all the oxybenzone has dissolved. Add the oil phase to the water phase and mix with a high speed disperser for a minimum of 15 minutes. Combine the water and TEA of Part of "C" and mix, then add the Colafax CPE and heat to 140–145 F while mixing until all has dissolved. The solution should be clear. Change to a 3 blade prop and continue mixing primary emulsion of Step 03. Add the TEA/Colafax CPE solution of Step 04 to the primary emulsion and mix for 3 minutes. Q.S. the batch to weight with the water of part D and mix well.

I claim:

1. An emulsion formulation for topical application to the skin comprising: an aqueous phase, an oil phase, at least one emulsifier, and a highly branched $C_{15}$ polyalphaolefin having a number average molecular weight of about 1000 to 5000, a polydispersity index of molecular weight to molecular number of about 0.01 to about 5, wherein the polyalphaolefin has water proofing capabilities.

2. The formulation of claim 1, wherein the formulation is an oil-in water emulsion.

3. The formulation of claim 2, wherein the at least one emulsifier is present in an amount of about 0.05 to about 20 percent by weight.

4. The formulation of claim 1, wherein the formulation is a water-in-oil emulsion.

5. The formulation of claim 4, wherein the at least one emulsifier is present in an amount of about 0.05 to about 20 percent by weight.

6. The formulation of claim 1, wherein the polyalphaolefin is present in an amount of about 0.05 to about 10 percent by weight.

7. The formulation of claim 6, wherein the polyalphaolefin is present in an amount of about 3 percent by weight.

8. The formulation of claim 1, further comprising an epichlorohydrin cross-linked glyceryl starch.

9. The formulation of claim 8, wherein the epichlorohydrin cross-linked glyceryl starch is present in an amount of about 0.1 to about 10 percent by weight.

10. The formulation of claim 1, further comprising at least one sunscreen active agent.

11. An emulsion formulation for topical application to the skin comprising: an aqueous phase, an oil phase, at least one emulsifier, an epichlorohydrin cross-linked glyceryl starch, a highly branched $C_{15}$ polyalphaolefin having a number average molecular weight of about 1000 to 5000, a polydispersity index of molecular weight to molecular number of about 0.01 to about 5, wherein the polyalphaolefin has water proofing capabilities, and at least one sunscreen active agent.

12. The formulation of claim 11, wherein the formulation is an oil-in water emulsion.

13. The formulation of claim 12, wherein the at least one emulsifier is present in an amount of about 0.05 to about 20 percent by weight.

14. The formulation of claim 11, wherein the formulation is a water-in-oil emulsion.

15. The formulation of claim 14, wherein the at least one emulsifier is present in an amount of about 0.05 to about 20 percent by weight.

16. The formulation of claim 11, wherein the polyalphaolefin is present in an amount of about 0.1 to about 10 percent by weight.

17. The formulation of claim 16, wherein the polyalphaolefin is present in an amount of about 3 percent by weight.

18. The formulation of claim 11, further comprising an epichlorohydrin cross-linked glyceryl starch.

19. The formulation of claim 18, wherein the epichlorohydrin cross-linked glyceryl starch is present in an amount of about 0.1 to about 10 percent by weight.

20. An after sun emulsion formulation for topical application to the skin comprising an aqueous phase, an oil phase, at least one emulsifier, a highly branched $C_{15}$ polyalphaolefin having a number average molecular weight of about 1000 to 5000, a polydispersity index of molecular weight to molecular number of about 0.01 to about 5, wherein the polyalphaolefin has water proofing capabilities.

21. An emulsion formulation for topical application to the skin comprising an aqueous phase, an oil phase, at least one emulsifier, a highly branched $C_{15}$ polyalphaolefin having a number average molecular weight of about 1000 to 5000, a polydispersity index of molecular weight to molecular number of about 0.01 to about 5, wherein the polyalphaolefin has water proofing capabilities, and an insect repellant.

22. An emulsion formulation for topical application to the skin comprising an aqueous phase, an oil phase, at least one emulsifier, a highly branched $C_{15}$ polyalphaolefin having a number average molecular weight of about 1000 to 5000, a polydispersity index of molecular weight to molecular number of about 0.01 to about 5, wherein the polyalphaolefin has water proofing capabilities, at least one sunscreen active agent and an insect repellant.

23. An emulsion formulation for topical application to the skin comprising an aqueous phase, an oil phase, at least one emulsifier, a highly branched $C_{15}$ polyalphaolefin having a number average molecular weight of about 1000 to 5000, a polydispersity index of molecular weight to molecular number of about 0.01 to about 5, wherein the polyalphaolefin has water proofing capabilities, and a sunless tanning agent.

* * * * *